United States Patent
Bowen et al.

(10) Patent No.: US 6,715,341 B2
(45) Date of Patent: Apr. 6, 2004

(54) PERMEABILITY MEASUREMENT APPARATUS AND METHOD

(75) Inventors: David Gordon Bowen, Jakarta Selatan (ID); Brian George Davidson Smart, Kinross (GB); James McLean Somerville, Stirling (GB)

(73) Assignee: Heriot-Watt University, Scotland (GB)

( * ) Notice: Subject to any disclaimer, the term of this patent is extended or adjusted under 35 U.S.C. 154(b) by 0 days.

(21) Appl. No.: 10/155,232

(22) Filed: May 28, 2002

(65) Prior Publication Data

US 2002/0189325 A1 Dec. 19, 2002

(30) Foreign Application Priority Data

May 26, 2001 (GB) .............................. 0112903

(51) Int. Cl.$^7$ .............................................. G01N 15/00
(52) U.S. Cl. ...................................................... 73/37; 73/38
(58) Field of Search ........................................ 73/37, 38

(56) References Cited

U.S. PATENT DOCUMENTS 4,555,934 A * 12/1985 Freeman et al. ............... 73/38
5,010,776 A * 4/1991 Lucero et al. ............. 73/863.23
5,750,996 A * 5/1998 Drennen et al. .......... 250/341.2

* cited by examiner

Primary Examiner—Hezron Williams
Assistant Examiner—André K. Jackson
(74) Attorney, Agent, or Firm—Venable LLP; Catherine M. Voorhees

(57) ABSTRACT

The present invention provides an apparatus for use in measuring permeability of a material. The apparatus 1 comprises a non-contact probe 6 comprising an inner pipe 8 and an outer pipe 10 which are arranged coaxially; a gas inlet for admitting a flow of gas into a first space 9 defined between the inner and outer pipes; and pressure difference measuring systems DP for measuring a pressure difference $\Delta P$ between said first space (P1) and a second space (P2) comprising the interior of the inner pipe 8. The probe 6 is mounted on a moveable head assembly 11 and the apparatus 1 further includes a position control system 12, 22 for controlling the movement of the head assembly 11 so as to cause the probe 6 to scan across a surface 2 of the material to be analysed, while maintaining the probe 6 at a constant distance Z from said surface 2, and for collecting pressure difference $\Delta P$ measurements, using said pressure difference measuring device DP during scanning movement of the probe 6.

18 Claims, 4 Drawing Sheets

PERMEABILITY MEASUREMENT APPARATUS AND METHOD

BACKGROUND OF THE INVENTION

This invention relates to a measurement apparatus and a method of measuring the gas permeability of rock and other geological materials. In particular, though not exclusively, the invention is for use in the petroleum, geotechnical, built environment and groundwater industries.

The measurement of rock permeability, porosity and fluid saturation from core samples in oil and gas exploration work gives vital information of the state of the reservoir under consideration, its potential flow capacity and can also provide insight into the most efficient methods of oil and/or gas extraction. Taking measurements of the gas permeability of rocks provides a method of classification of the rock type and quality. Permeability data are used both as absolute values and to provide correlation statistics.

At present, permeability has been measured utilising either a core plug drilled from the rock sample at predetermined intervals, or by a contact method. For contact methods a probe is normally used. The probe is commonly in the form of a pipe having an orifice of known diameter at one end, with a sealing ring at this end for forming a seal with the surface with which the probe end makes contact. In use, the probe end is placed in direct contact with the rock whose permeability is to be measured. A fixed rate flow of gas is then flowed through the pipe (at either a predetermined or continuously varying pressure). A pressure drop is caused by gas entering the rock, the pressure drop being dependent on the, permeability of the rock.

Point sampled measurements of this pressure drop can be used to obtain a measure of the local permeability of the rock material.

The main problem with such contact measurement methods is the errors produced by variation of the coupling of the probe to the rock, and statistical errors induced by an inappropriate sampling regime when the natural heterogeneity of the rock material and/or its surface is considered. Both the volume of rock being investigated, its relationship to the theoretical statistical support volume and the restrictive frequency of the point sampling nature of these experiments, lead to potential aliasing of the frequency of natural geological variability, and have thus inhibited the utility and application of the method. With core plug sampling these potential errors are compounded by the enforcing of a strict one-dimensional pressure field upon the sample. The currently used methods are also very time consuming since the probe needs to be lifted up and down (i.e. out of contact with the sample and back into contact with the sample) between each measurement.

SUMMARY OF THE INVENTION

The present invention seeks to avoid or minimise one or more of the foregoing disadvantages. In particular, the invention seeks to increase accuracy of the measurement of the permeability, while also speeding up data acquisition.

Accordingly, the present invention provides an apparatus suitable for use in measuring permeability of a material, the apparatus comprising: a non-contact probe comprising a first conduit and a second conduit which are arranged so that their open ends are contiguous; a gas inlet for admitting a flow of gas into a first space inside said first conduit; and a pressure difference measuring system for measuring a pressure difference between said first space and a second space inside said second conduit; wherein there is provided a probe support formed and arranged for supporting the open end of the probe at a predetermined height above a surface of said material, in use of the apparatus; and wherein said apparatus includes processor means programmed for converting a said pressure difference measurement into a permeability value, in use of the apparatus. Normally the second conduit would be blind i.e. the end remote from its open end, would be closed.

Various different forms of conduits may be used in the apparatus of the invention. Advantageously, the conduits are configured so as to provide a relatively large degree of contiguity therebetween. Conveniently the conduits are configured so that one of said conduits extends along opposite sides of the other conduit. Most conveniently one of said conduits surrounds the other conduit, said conduits being defined by substantially coaxial pipes. Other possible configurations comprise coaxial elongate, generally slot-form, rectangular cross-section pipes. Where coaxial pipes are used, it will be appreciated that either the outer or the inner conduit may be used for the gas supply.

In a particularly simple form of the invention, the probe support comprises a spacer element projecting below the open end of the probe whereby said open end may be held above the material surface by contacting the spacer with the material surface.

Advantageously the probe is mounted on a moveable head assembly and the apparatus further includes a position control system formed and arranged for controlling the movement of the head assembly so as to cause the probe to scan across a surface of the material to be analysed, in use of the apparatus, while maintaining the probe at a constant distance from said surface, whereby pressure difference measurements from a plurality of points across said surface, using said pressure difference measuring system, may be readily collected by scanning of said surface by said probe.

Thus, in a preferred aspect the present invention provides an apparatus suitable for use in measuring permeability of a material, the apparatus comprising: a non-contact probe comprising an inner pipe and an outer pipe which are arranged coaxially; a gas inlet for admitting a flow of gas into a first space defined between the inner and outer pipes; and a pressure difference measuring system for measuring a pressure difference between said first space and a second space comprising the interior of the inner pipe; wherein the probe is mounted on a moveable head assembly and the apparatus further includes a position control system formed and arranged for controlling the movement of the head assembly so as to cause the probe to scan across a surface of the material to be analysed, in use of the apparatus, while maintaining the probe at a constant distance from said surface, for collecting pressure difference measurements from a plurality of points across said surface, using said pressure difference measuring system, during scanning of said surface by said probe.

The control means preferably includes a distance-measuring means i.e. rangefinder device for measuring, preferably substantially continuously in time, the separation between the probe and the surface of the material being analysed i.e. the height of the probe above the surface. The distance measuring means preferably provides a feedback signal, representing the amount of any change in said measured distance, to the control means which is adapted to control the spacing of the head assembly from the surface of said material so as to maintain the probe at a constant height above the surface of said material. Preferably, the distance-measuring means is a distance-measuring laser.

In general the apparatus is formed and arranged so that the probe is supported at from 0.1 to 0.5 mm above the material surface, advantageously from 0.2 to 0.3 mm above the surface. It is important that the probe end is supported at a constant height above the material surface. Preferably the height should be kept with +/−10%, most preferably +/−5%, desirably +/−3% of a predetermined height. It is generally preferred though to limit the size of the probe and diameter in order to maintain a reasonable spatial resolution for permeability measurements across the surface of the material. Typically there is used an overall probe end diameter in the range from 2 to 5 mm.

The apparatus may include a data processing device for calculating a value representing the permeability of said material to said gas, for each collected pressure difference measurement, and preferably immediately following collection of that pressure difference measurement. Alternatively said values representing permeability may be calculated for a multiplicity of pressure difference measurements subsequent to the collection of all of said multiplicity of pressure difference measurements.

The apparatus preferably further includes a memory or other storage device for storing the collected pressure difference measurements and/or the calculated values representing permeability, together with respective surface position information associated therewith. This enables the variation in permeability across the area of the surface of the material to be subsequently mapped out. The apparatus may conveniently include a computer device programmed so as to generate a map of the permeability and for displaying said map on a visual display unit which may be connected to the processor in use of the apparatus.

Preferably, the position control system comprises at least one positioning device, the or each said positioning device comprising at least one of a precision linear-scale slide and a stepper motor, with an associated control device therefor.

As noted above, a particular benefit of the invention is the contactless nature of the probe used and the speed of operation of the apparatus. These benefits can advantageously be significantly extended by providing at least one contactless measuring device on the moveable head assembly of the apparatus, for making measurements of other material properties at the same time. Thus, for example, the apparatus may also include at least one laser for use in making acoustic property measurements for use in determining physical properties such as Young's modulus. In this approach the surface is subjected to a high-energy laser burst, which creates a shock wave in the material. The amplitude and velocity of this shock-wave can be sensed utilising a laser (preferably a second laser) monitoring the surface wave's amplitude by either reflection triangulation (which is described in further detail later) or, preferably, by interferometry of the light wavelength.

Preferably, the apparatus may also include at least one laser measuring device formed and arranged for measuring the height of a point on said surface relative to a predetermined datum, for use in making surface roughness measurements.

Surface roughness measurements can be of particular value in the context of the present invention, since the flow of fluid through rock strata is, in practice, usually dependent on both the permeability of the material and the conductivity of the material which is flow or transport of fluid through cracks in the material. The latter is increasingly dependent on the surface roughness of the opposed faces of the material which define a crack in the material, as the thickness of the crack reduces.

Preferably, the apparatus may also include at least one laser formed and arranged for volatilising material from a point on said surface, and a spectrometer associated therewith, for carrying out analysis of the constituent components of the material being analysed. Preferably, the spectrometer is a mass spectrometer or an infrared spectrometer.

In a further aspect the present invention provides a method of measuring permeability of a material, comprising the steps of:

a) providing an apparatus according to claim 1;

b) passing gas through said first space towards the surface of said material, at a predetermined flowrate;

c) supporting the probe end at a fixed distance from the surface of the material;

d) measuring a pressure difference between said first space and said second space so as to obtain a pressure difference measurement; and e) determining a permeability value for the pressure difference measurement.

According to a second preferred aspect of the invention, there is provided a method of measuring permeability of a material, comprising the steps of:

a) providing a probe comprising an inner pipe and an outer pipe arranged coaxially, and positioning the probe substantially perpendicularly to a surface of a material to be analysed;

b) passing gas through a first space defined between the inner and outer coaxial pipes, towards the surface of said material, at a predetermined flowrate;

c) scanning the probe across the surface of said material, while also maintaining the probe at a fixed distance from the surface of the material;

d) measuring a pressure difference between said first space defined between said inner and outer pipes, and a second space comprising the interior of said inner pipe, at a plurality of different points across said surface of the material; and e) determining a permeability value for the pressure difference measurement at each said point.

The pressure difference measurements are preferably collected at lateral distance intervals of from a minimum of about 20 μm to any user defined maximum interval, during the lateral movement of the probe.

Alternatively, the pressure difference measurements could be collected at predetermined time intervals, for example every 0.1 seconds, during the lateral scanning movement of the probe at a predetermined rate across the material surface, typically there may be used a scanning speed from 0.1 to 10 cm sec$^{-1}$, conveniently about 1 cm sec$^{-1}$.

Preferably, the method further comprises the step of f) measuring one or more other properties of the material using one or more devices selected from the group of: a laser with sensor for making surface roughness measurements; at least one laser for making acoustic property measurements; and a laser and a spectrometer for analysing constituent components of the material.

Any suitable form of sample having generally level surface may be used in the method of the invention. Conveniently though there is used a longitudinally sliced slab from a cylindrical core sample. Typically such a slab might be 20×8×1 cms in size.

BRIEF DESCRIPTION OF THE DRAWINGS

Preferred embodiments of the present invention will now be described, by way of example only, and with reference to the accompanying drawings in which.

DETAILED DESCRIPTION OF THE INVENTION

Figure 1:
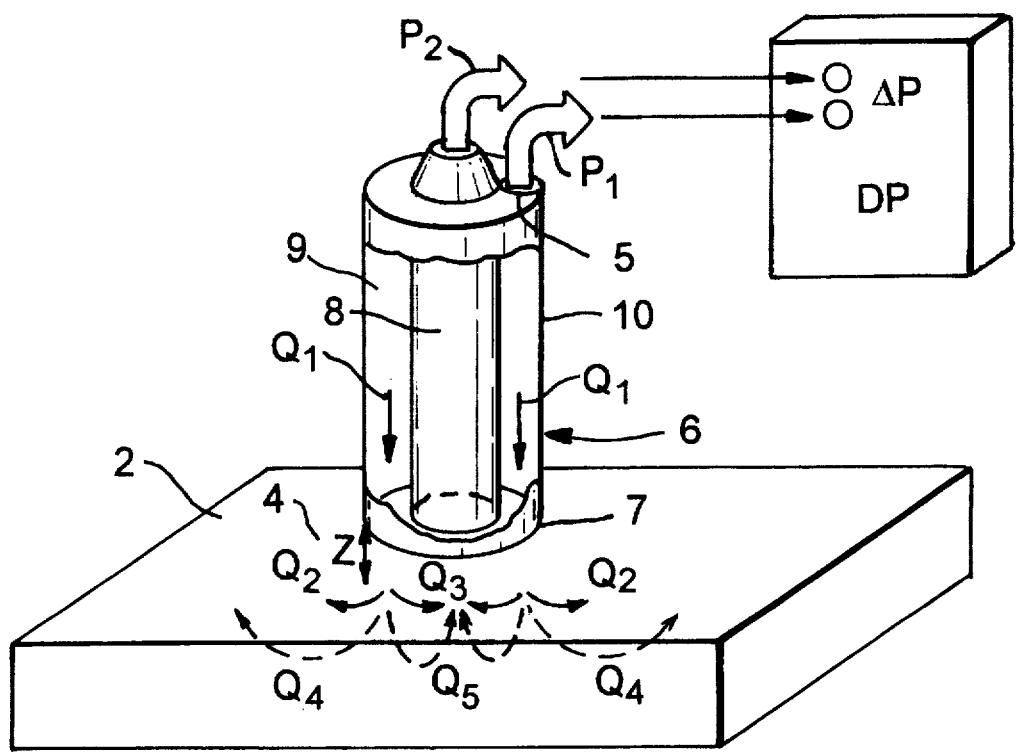
FIG. 1 is a schematic diagram of a coaxial non-contact probe of a permeability measuring apparatus of the invention, positioned above a surface to be analysed.

FIG. 1 shows a non-contact coaxial probe 6 of a permeability measuring apparatus of the invention, positioned perpendicularly to and above a surface 2 of a slab of material 4 the permeability of which is to be measured. The probe 6 is positioned so that a lower end 7 thereof is at a fixed distance Z above the surface 2 of the material. As can e seen from FIGS. 1, and 1A the coaxial probe 6 comprises an inner pipe 8 and an outer pipe 10. Dry Nitrogen Gas, under controlled pressure of between 0.5 and 1.5 Bar, is passed via an inlet 5 down through the outer pipe 10 (in the space 9 defined between the two pipes) towards the surface 2 of the material, at a fixed flow rate Q1. Both the pressure of the gas P1 in the space 9 defined between the inner and outer pipes 8,10 and the pressure P2 in the inner pipe 10 are sensed, and measured by a precision semiconductor pressure sensor DP. The pressure sensor DP is driven by a suitable input voltage and provides a DC voltage analogue output representing the pressure difference $P_1-P_2$. Since the probe 6 is perpendictilar to the surface 2 of the material, there will be a steady-state flow Q2 of Nitrogen gas outward and above the surface, and Q3 inward above the surface. There will also be flows of Nitrogen into the material both inward Q5 towards the inner pipe 10 and outwards Q4 from the probe 6. The relative values of Q2, Q3, Q4 and Q5 are dependant upon the permeability of the material. In this configuration, the pressure differential ΔP between the pressures in the inner and outer coaxial pipes 8, 10: $P_2$ and $P_1$, respectively, is created by the difference between Q3+Q5 and Q1.

Continual measurement of this pressure drop (ΔP) whilst maintaining the probe 6 at a constant distance Z from the material surface 2 allows the permeability, k, at any given position on the material surface to be determined by virtue of the dependence of the respective flow rates of gas on the permeability of material, and hence the size of the gas flow rate through the material.

Figures 1A, 1B:
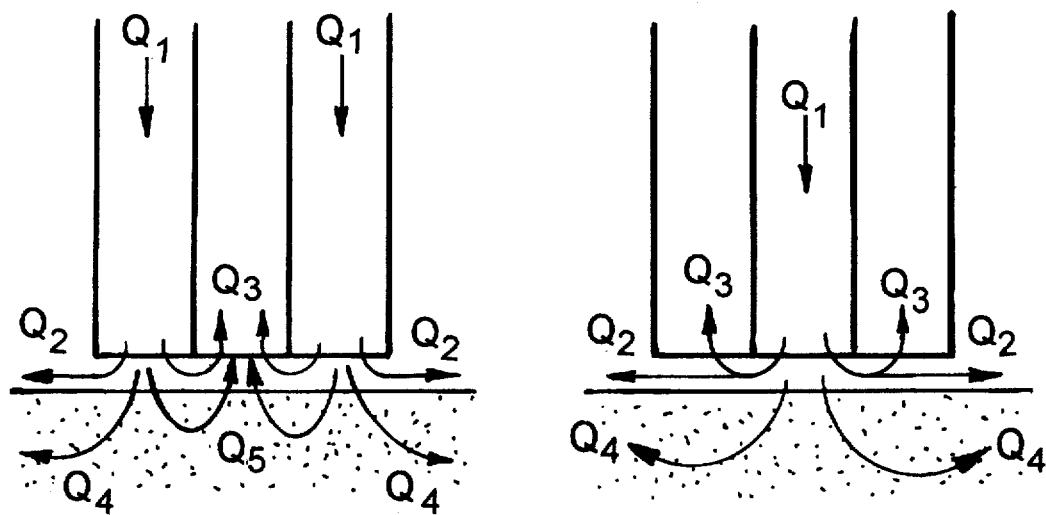
FIG. 1A is a detail sectional view of part of FIG. 1 showing the relation of the probe to the sample surface.
FIG. 1B is a corresponding view of a modified embodiment.

In an alternative form of apparatus, the Nitrogen gas is fed through the inner coaxial pipe 8, as shown in FIG. 1B.

As in the case of the previous mode, there will be a steady-state flow Q2 of Nitrogen gas outward and above the surface, with some flow Q3 into the outer coaxial pipe. There will also be a flow Q4 into the material. (In this case the flow from the material up into the outer pipe—corresponding to Q5, would normally be more or less negligible). The relative values of Q2, Q3 and Q4 are again dependant upon the permeability of the material. The pressure differential ΔP between the inner and outer coaxial pipes is created by the difference between Q1 and Q3, in the inner and outer coaxial pipes 8, 10. Continual measurement of this pressure drop (ΔP) whilst maintaining the probe 6 at a constant distance Z from the material surface 2 allows the permeability, k, at any given position on the material surface to be determined by virtue of the dependence of the respective flow rates of gas on the permeability of material, and hence the size of the gas flow rate through the material.

Conventionally the permeability of a porous material sample is measured by passing a gas flow Q ($cm^3$/sec) from one end of a sample of constant cross-sectional area A ($cm^2$) and length 1 (cm) to its other end, and measuring the pressure differential ΔP (bar) across the two ends. The permeability k (Darcy) is then given by Darcy's equation:

$$k = \frac{Q \cdot \mu \cdot l}{A \cdot \Delta P}$$

where μ is the viscosity of the gas (in cP) and the other terms have the above-indicated meanings. In the case of the present invention it will be appreciated that although the flow of gas through the material is governed by the same equation, the relationship between the measured pressure differential ΔP ($=P_1-P_2$) and permeability k, is somewhat more complex than can be represented by such a simple equation because of the various different flow paths available to the input gas flow $Q_1$. in practice therefore one would normally calibrate the apparatus using a plurality of synthetic porous media (typically ceramic) samples of substantially constant known permeability (determined using conventional known techniques) of different values. (Such samples are readily available commercially in the ceramic filter industry and the like.)

Continuously moving the probe 6 across the sample, while keeping the distance Z of the probe 6 from the surface 2 constant, and using conventional X-Y raster scan point sampling of the material's permeability at regularly spaced intervals in the lateral movement of the probe, enables a mapping of the variation in permeability to be compiled.

Figure 2:
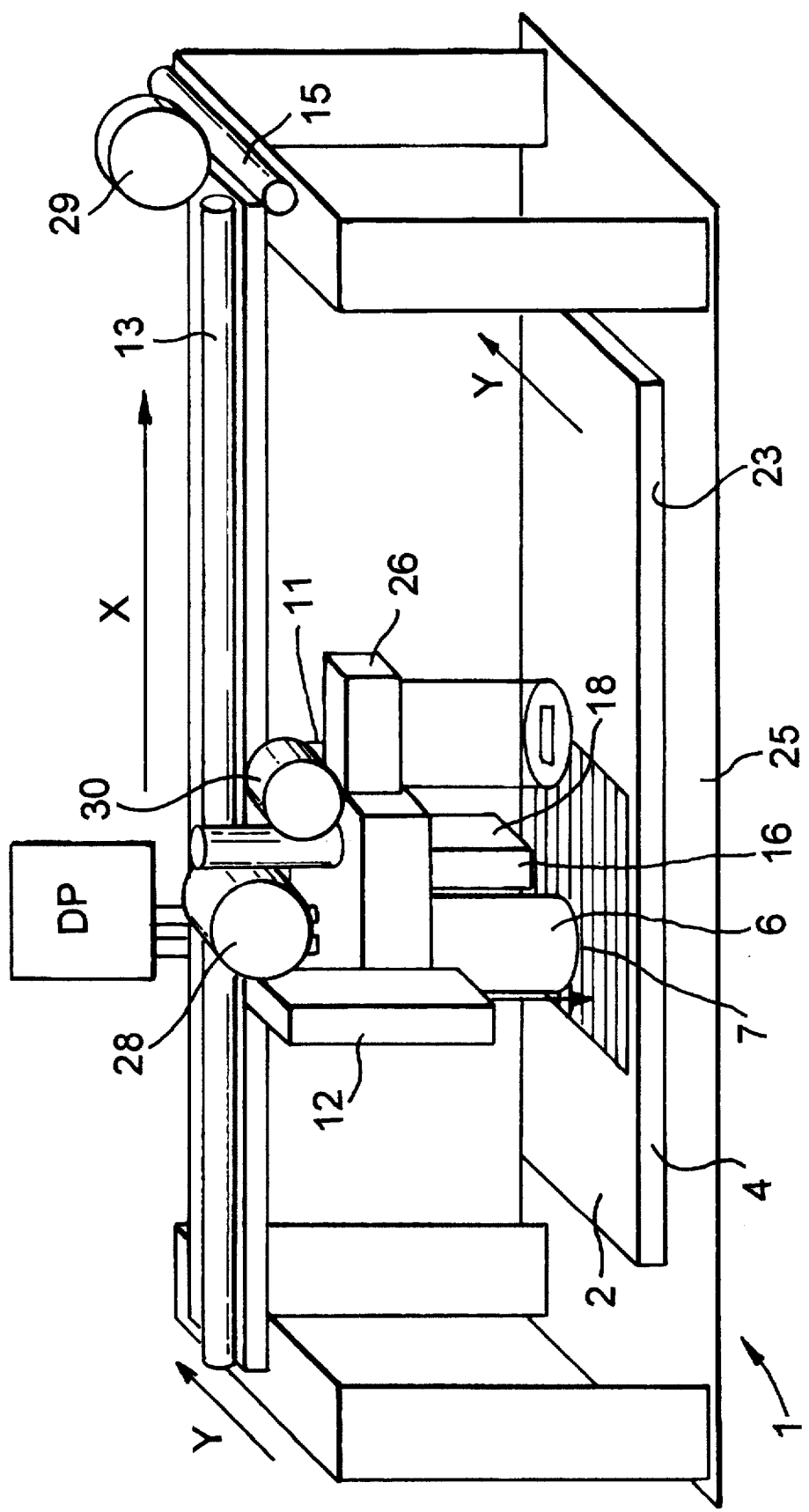
FIG. 2 is a schematic perspective view of a permeability-mapping measuring apparatus according to another embodiment.

In order to maintain the probe at the fixed distance Z from the surface 2 of the material it will be appreciated that the probe needs to be moved (vertically) up and down relative to the surface 2 in order to compensate for variations (in height) present in the surface of the material. To achieve this, a distance-measuring laser device 12 is used in conjunction with the coaxial probe 6. The probe and the distance-measuring device 12 are mounted together in a head assembly 11, of a permeability apparatus 1 of the invention, as shown in FIG. 2. Thus, the distance-measuring device moves laterally with the probe 6 (relative to the surface 2). The distance-measuring device is used in a closed-loop feedback control manner in conjunction with a computer controller 22 connected to both the probe 6 and laser device 12 (see FIG. 3) to control the distance of the probe 6 from the surface 2. The feedback signals (in the form of error signals representing change in the height of the head assembly relative to the surface 2) from the distance-measuring device 12 to the computer controller 22 provide a mapping of the topography of the surface 2 and are acquired simultaneously with each measurement of the pressure drop ΔP.

This measurement of the topography of the surface 2 is useful in the interpretation of the permeability data. The feedback signals are also used by the computer controller 22 to adjust the height of the head assembly 11 so as to maintain the distance Z between the end of the probe and the surface 2 (as measured by the laser device 12), at a constant value. It will be appreciated that the laser device 12 is positioned relative to the probe (in the head assembly 11) so as to measure the distance to an area of the surface 2 immediately ahead of the probe 6 in the path of the moving probe 6.

The computer controller 22 also controls the lateral movement of the probe 6.

Positioning equipment is provided, under the control of the computer controller 22, for controlling the lateral movement of the probe. The positioning equipment comprises linear X and Y scale slides 13, 15 and three precision stepper motors 28,29,30 which are linked to the head assembly 11 for driving the head assembly laterally 28,29 over the material surface 2, and controlling 30 the height of the head assembly 11 relative to the surface 2 of the material.

FIG. 2 shows the apparatus in use, with a slab of core material 4 placed within a sample holder slot 23 of a sample material mounting base 25. The desired maximum and minimum X,Y co-ordinates for the area of the surface 2 of the material to be scanned by the probe are entered (digitally) by the operator to the computer controller 22 by locating the desired X,Y co-ordinate positions with the laser spot from the positioning laser device 12. The entry of these maximum and minimum X,Y positions initialises a computer control program loaded in the computer controller 22 which then causes the probe 6 to scan the surface 2 of the material. An acquisition protocol included in the computer control program causes data to be recorded from the probe at regularly spaced spans in the lateral movement of the probe, typically every 40 μm (microns) of travel. The recorded data includes the pressure difference measurement $\Delta P = P_1 - P_2$, the distance Z of the end of the probe from the surface 2 and the input gas flow rate $Q_1$. Multi channel acquisition circuitry is included in the controller 22 for collecting this data, together with the respective spatial location parameters (i.e. X and Y co-ordinates for each set of data collected at a given position of the probe). The controller continues to scan the surface 2 with the probe, collecting data in this manner, until the whole of the area initially specified by the operator has been scanned. The controller 22 stores the collected data in a memory (not shown separately) which is provided for this purpose. An analyser 24 (for example a suitable microprocessor) is provided for analysing the data collected by the controller 22 from the probe 6. The analyser 24 may be separate from the controller 22, or integrated with it, and may incorporate the memory in which the collected data is stored. The analyser is programmed to calculate a map of the variation in ΔP over the surface 2 of the material (which can be interpreted as measure of the variation in the permeability k over the surface 2).

The pressure difference measurements ΔP (from the pressure sensor DP) can be improved through application of mathematical filters. The output of a laser 20 measuring surface roughness (see below) can be transformed to provide a Fourier spectrum of the surface roughness. This may be used as a filter to refine the ΔP data by simple subtraction of the corresponding Fourier transform of ΔP. This approach can extend the application to more rough surfaces than would otherwise be possible.

Figure 4:
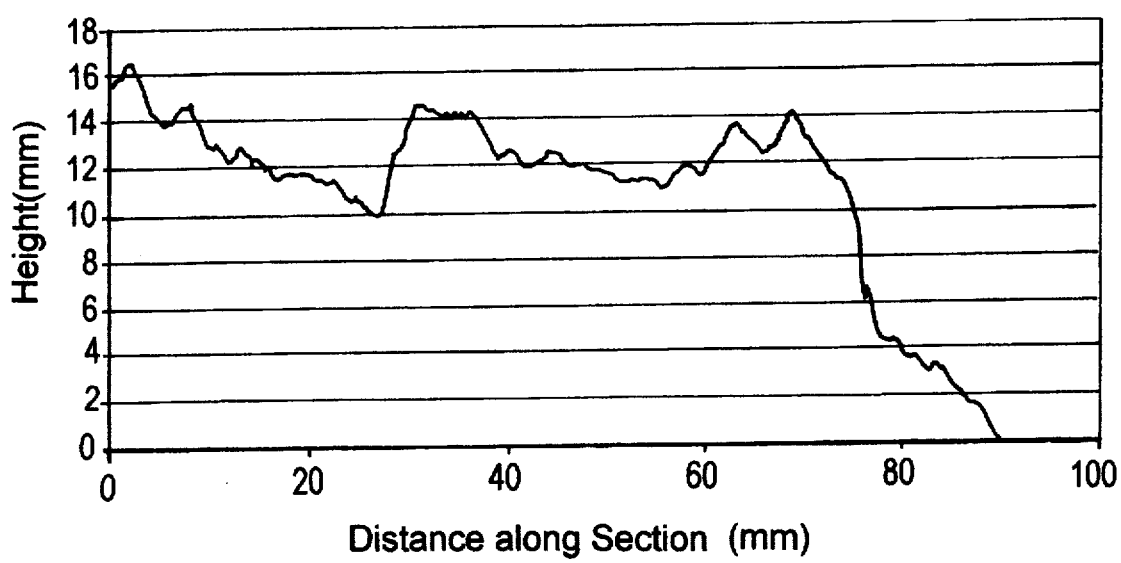
FIG. 4 is a typical surface profile obtained using the surface profile measuring facility provided in the apparatus of FIG. 2.
Figure 5A:
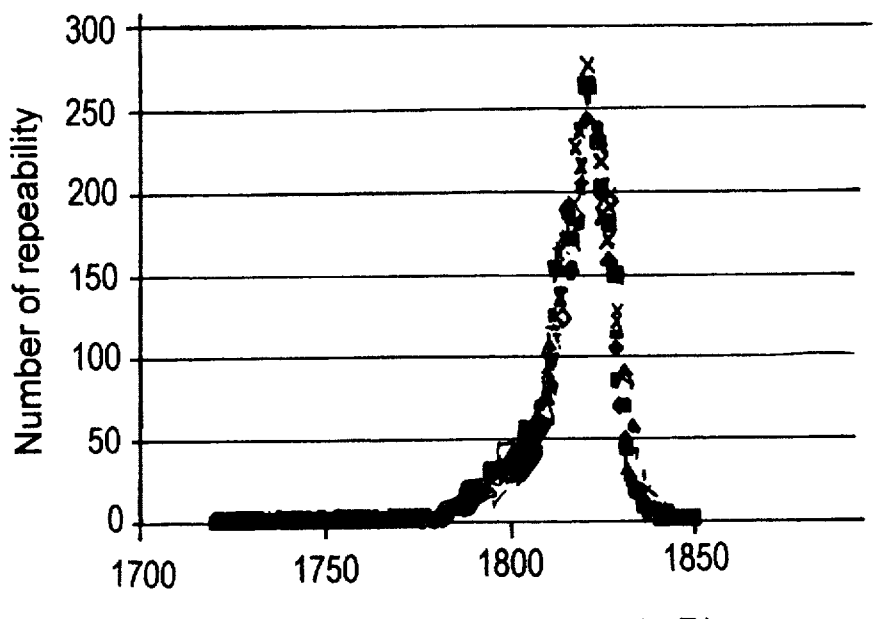
FIGS. 5A and 5B are plots representing permeability measurements obtained with an apparatus of the invention and with a known apparatus.
Figure 5B:
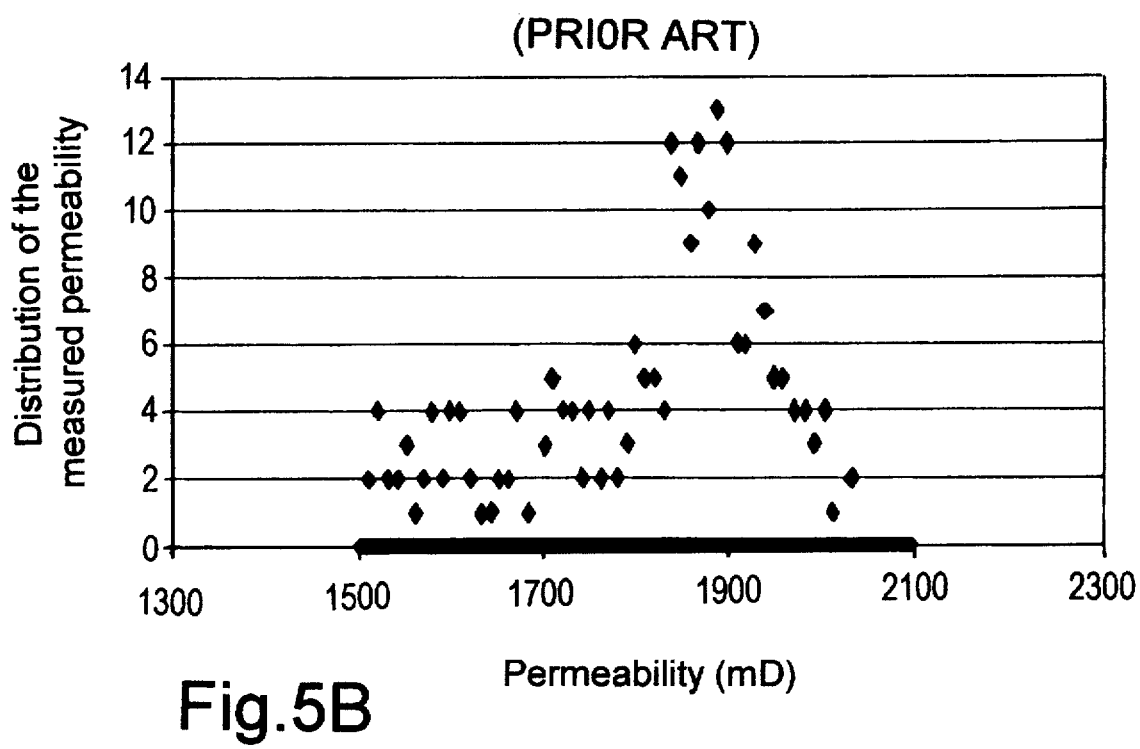

A typical single axis surface profile of a fractured rock core sample surface is shown in FIG. 4. It will be appreciated that it would be extremely difficult to obtain any reliable permeability measurements of a sample with such a rough surface, using conventional direct-contact permeability measurement apparatus. The high reliability of the permeability measurements obtainable using the present invention is indicated by FIGS. 5A and 5B which compare typically obtained results from the method of the present invention and from a known apparatus.

In a modified version of the above-described embodiment the analyser 24 is also programmed to calculate a value for the permeability k for each ΔP measurement and the corresponding flow Q1 of gas into the probe, using Darcy's equation (see above). A value of Q3 would be obtained using calibration, by reference to measurements (taken with the above-described apparatus) of the pressure difference ΔP on a blank standard (i.e. a predetermined surface) known to have zero permeability and on another predetermined surface known to have a high permeability, for a known flow rate Q1 of gas into the probe. Form these measurements it will be appreciated that a value for the returning volume Q3+Q5 or Q3 can thus be calibrated for each measured ΔP value on the test material surface 2, thus enabling a corresponding value of the permeability k, to be calculated from Darcy's equation.

In this modified embodiment the analyser 24 is programmed to create a map of the variation in permeability k over the surface 2 of the material being analysed, using the calculated values of k and the associated surface position data.

Figure 3:
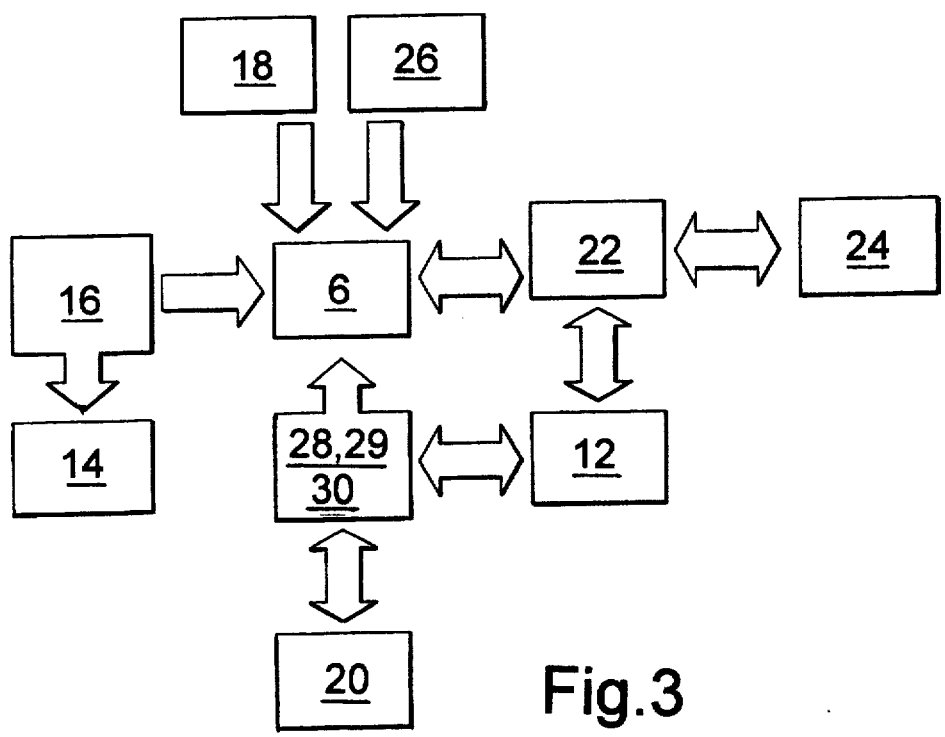
FIG. 3 is a schematic block diagram of a measuring apparatus according to one embodiment of the invention.

FIG. 3 shows a block diagram of the apparatus of FIG. 2, further including additional measurement devices (mounted in the head assembly 11) which may be used in conjunction with the coaxial probe 6 to determine other properties of the material, such as the porosity and the acoustic nature of the material.

To determine the acoustic properties of the material, one or more additional lasers 18 are provided. The surface 2 is subjected to a high-energy laser burst from a first laser (this may be a laser specifically provided for this purpose, or a laser already present in the system for another purpose) which creates a shock wave in the material. The amplitude and velocity of this shock-wave is sensed utilising a second laser 18 monitoring the surface wave's amplitude by reflection triangulation, whereby the laser light is emitted from a device coupled with its own photoelectric sensing aperture, arranged at a small angle to the lased light ray-path, such that a triangulation of emitted ray-path can be used to calculate the distance of the laser light spot on the material from the sensor. Alternatively, interferometry of the light wavelength can be used to monitor the surface-wave's amplitude with an interferometer 26. (This is the generally preferred method.)

Surface roughness measurements of the surface 2 may be taken using an additional laser sensor 20 which is optionally provided for this purpose. In this approach the laser light is emitted from a laser device (provided in the apparatus) coupled with its own photoelectric sensing aperture arranged at a small angle to the lased light ray-path, such that a triangulation of emitted ray-path can be used to calculate the distance of the laser light spot on the material from the sensor. Alternatively, should the processing allow it, surface roughness measurements may be taken from the topographic distance measurements obtained from the laser device 12.

An analysis of the constituent components of the material can also be obtained by emitting a burst of laser light from a further laser 16 provided for this purpose, in order to vaporise a small spot of the surface 2. The vapour is then analysed by a spectrometer 14, which may be a mass spectrometer or infrared spectrometer, or any other suitable analysing device.

What is claimed is:

1. An apparatus suitable for use in measuring permeability of a material, the apparatus comprising: a non-contact probe comprising a first conduit and a second conduit which are arranged so that their open ends are contiguous; and form an open end of the probe: a gas inlet for admitting a flow of gas into a first space inside said first conduit; and a pressure difference measuring system for measuring a pressure difference between said first space and a second space inside said second conduit; wherein there is provided a probe support formed and arranged for supporting the open end of the probe at a predetermined height above a surface of said material; and wherein said apparatus includes processor means programmed for converting a said pressure difference measurement into a permeability value.

2. An apparatus according to claim 1 wherein said conduits are defined by coaxial pipes.

3. An apparatus suitable for use in measuring permeability of a material, the apparatus comprising: a non-contact probe comprising an inner pipe and an outer pipe which are arranged coaxially; a gas inlet for admitting a flow of gas into a first space defined between the inner and outer pipes; and pressure difference measuring system for measuring a pressure difference between said first space and a second space comprising the interior of the inner pipe; wherein the probe is mounted on a moveable head assembly and the apparatus further includes a position control system formed and arranged for controlling the movement of the head assembly so as to cause the probe to scan across a surface of the material to be analysed, while maintaining the probe at a constant distance from said surface, for collecting pressure difference measurements from a plurality of points across said surface, using said pressure difference measuring system, during scanning of said surface by said probe.

4. An apparatus according to claim 3 wherein the control system includes a rangefinder device for measuring the separation between the probe and the surface of the material being analysed.

5. An apparatus according to claim 4 wherein said control system includes a separation control device coupled to said rangefinder device so as to maintain the probe at said constant distance from said surface of said material.

6. An apparatus according to claim 5 wherein said range finder device is a distance-measuring laser.

7. An apparatus according to claim 3 wherein said position control system comprises at least one positioning device, with said at least one positioning device comprising at least one of a precision linear-scale slide and a stepper motor, with an associated control device therefore.

8. An apparatus according to claim 3 which includes a data processing device for calculating a value representing the permeability of said material to said gas, from said collected pressure difference measurements.

9. An apparatus according to claim 8 which includes a memory device for storing at least one of the collected pressure difference measurements and the calculated values representing permeability, together with respective surface position information associated therewith.

10. An apparatus according to claim 8 which includes a computer device programmed so as to generate such a map of the permeability of said material across said surface.

11. An apparatus according to claim 3 wherein there is provided at least one contactless measuring device on the moveable head assembly of the apparatus for use in making measurements of one or more other material properties.

12. An apparatus according to claim 11 which includes as least one laser measuring device formed and arranged for measuring the height of a point on said surface relative to a predetermined datum, for use in making surface roughness measurements.

13. An apparatus according to claim 11 which includes at least one laser formed and arrange for volatilising material from a point on said surface, and a spectrometer associated therewith, for carrying out analysis of the constituent components of the material being analysed.

14. An apparatus according to claim 13 wherein said spectrometer is a mass spectrometer or an infrared spectrometer.

15. An apparatus according to claim 11 which includes at least one laser formed and arranged for creating a shock wave in the material, and includes a laser device formed and arranged for sensing the amplitude and velocity of said shock-wave.

16. An apparatus according to claim 15 wherein said laser device is formed and arranged for monitoring the surface wave's amplitude by either reflection triangulation, or by interferometry of the light wavelength.

17. A method of measuring permeability of a material, comprising the steps of:

a) providing an apparatus according to claim 1;

b) passing gas through said first space towards the surface of said material, at a predetermined flowrate;

c) supporting the probe end at a fixed distance from the surface of the material;

d) measuring a pressure difference between said first space and said second space so as to obtain a pressure difference measurement; and e) determining a permeability value for the pressure difference measurement.

18. A method of measuring permeability of a material, comprising the steps of:

a) providing a probe comprising an inner pipe and an outer pipe arranged coaxially, and positioning the probe substantially perpendicularly to a surface of a material to be analysed;

b) passing gas through a first space defined between the inner and outer coaxial pipes, towards the surface of said material, at a predetermined flowrate;

c) scanning the probe across the surface of said material, while also maintaining the probe at a substantially fixed distance from the surface of the material;

d) measuring a pressure difference between said first space defined between said inner and outer pipes, and a second space comprising the interior of said inner pipe, at a plurality of different points across said surface of the material; and e) determining a permeability value for the pressure difference measurement at each said point.

* * * * *

UNITED STATES PATENT AND TRADEMARK OFFICE
Certificate

Patent No. 6,715,341 B2                                                Patented: April 6, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Gordon Bowen, Jakarta Sefatan, Indonesia; Brian George Davidson Smart, Kinross, United Kingdom; James McLean Somerville, Stirling, United Kingdom; and Naim Wajih Al-Jabari, Abu Dhabi, United Arab Emirates.

Signed and Sealed this Twenty-eighth Day of June 2005.

HERZON E. WILLIAMS
*Supervisory Patent Examiner*
Art Unit 2856